US008063208B2

(12) United States Patent
Wei et al.

(10) Patent No.: US 8,063,208 B2
(45) Date of Patent: Nov. 22, 2011

(54) CRYSTALLINE FORMS OF (3R,4R)-4-AMINO-1-[[4-[(3-METHOXY-PHENYL)AMINO]PYRROLO[2,1-F][1,2,4]TRIAZIN-5-YL]METHYL]PIPERIDIN-3-OL

(75) Inventors: Chenkou Wei, Princeton Junction, NJ (US); Derek J. Norris, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 825 days.

(21) Appl. No.: 11/675,108

(22) Filed: Feb. 15, 2007

(65) Prior Publication Data
US 2007/0191375 A1 Aug. 16, 2007

Related U.S. Application Data

(60) Provisional application No. 60/773,923, filed on Feb. 16, 2006.

(51) Int. Cl.
C07D 401/12 (2006.01)
C07D 487/04 (2006.01)
A61K 31/53 (2006.01)
A61K 35/00 (2006.01)

(52) U.S. Cl. ......................... 544/183; 514/243
(58) Field of Classification Search .............. 544/183; 514/243
See application file for complete search history.

(56) References Cited

U.S. PATENT DOCUMENTS

| | | | |
|---|---|---|---|
| 6,670,357 B2 | 12/2003 | Leftheris et al. | |
| 6,787,545 B1 | 9/2004 | Ohtani et al. | |
| 6,867,300 B2 | 3/2005 | Godfrey, Jr. et al. | |
| 6,869,952 B2 | 3/2005 | Bhide et al. | |
| 6,908,916 B2 | 6/2005 | Mastalerz et al. | |
| 6,916,815 B2 | 7/2005 | Vite et al. | |
| 6,933,386 B2 | 8/2005 | Bhide et al. | |
| 6,951,859 B2 | 10/2005 | Bhide et al. | |
| 6,969,717 B2 | 11/2005 | Bhide et al. | |
| 7,030,118 B2 | 4/2006 | Lombardo et al. | |
| 7,064,203 B2 | 6/2006 | Gavai et al. | |
| 7,102,001 B2 | 9/2006 | Swaminathan et al. | |
| 7,102,002 B2 | 9/2006 | Cai et al. | |
| 7,102,003 B2 | 9/2006 | Gavai et al. | |
| 7,141,571 B2 | 11/2006 | Fink et al. | |
| 7,297,695 B2 * | 11/2007 | Fink et al. ............... | 514/243 |
| 2003/0232831 A1 | 12/2003 | Dyckman et al. | |
| 2004/0229877 A1 | 11/2004 | Leftheris et al. | |
| 2005/0182058 A1 | 8/2005 | Fink et al. | |

FOREIGN PATENT DOCUMENTS

| | | |
|---|---|---|
| EP | 0 713 876 | 5/1996 |
| WO | WO 98/08847 | 3/1998 |
| WO | WO 00/71129 | 11/2000 |
| WO | WO 02/40486 | 5/2002 |
| WO | WO 03/090912 | 11/2003 |
| WO | WO 2004/009784 | 1/2004 |

OTHER PUBLICATIONS

Cecil Textbook of Medicine, edited by Bennet, J.C., and Plum F., 20th edition, vol. 1, 1004-1010, 1996.*
Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys. vol. 58(3): 932-940, 2004.*
Fabbro et al. Pharmacology & therapeutics 93, 79-98, 2002.*
U.S. Appl. No. 60/620,784, filed Oct. 21, 2004, Gavai et al.
Ewald, H. et al., "Reaktionen von 1,2,4-Triazinen mit Acetylendicarbonsäure-dimethylester", Liebigs Ann. Chem., pp. 1718-1724 (1977).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-f]-1,2,4-triazine Derivatives", J. Heterocyclic Chem., vol. 16, pp. 833-834 (1979).
Neunhoeffer, H. et al., "Cycloadditionen mit Methoxy- und Dialkylamino-1,2,4-triazinen", Liebigs Ann. Chem., pp. 1413-1420 (1977).
Patil, S.A. et al., "Synthesis of Pyrrolo[2,1-f][1,2,4]triazine Congeners of Nucleic Acid Purines via the N-Amination of 2-Substituted Pyrroles", J. Heterocyclic Chem., vol. 31, pp. 781-786 (1994).
Quintela, J.M. et al., "A Ready One-pot Preparation for Pyrrolo[2,1-f][1,2,4]triazine and Pyrazolo[5,1-c]pyrimido[4,5-e]-[1,2,4]triazine Derivatives", Tetrahedron, vol. 52, No. 8, pp. 3037-3048 (1996).
Tsi-Ping et al., TIPS, vol. 16:5766 (1995).
de La Matte Rouge, Thibault et al., Cancer Research, vol. 67, No. 13, pp. 6253-6262 ( 2007).
http://Clinicaltrials.gov , Search Results for BMS-690514 (Dec. 22, 2008).

* cited by examiner

*Primary Examiner* — Venkataraman Balasubramanian
(74) *Attorney, Agent, or Firm* — Ying Wang

(57) ABSTRACT

Crystalline forms of (3R,4R)-4-amino-1-[[4-[(3-methoxyphenyl)amino]pyrrolo[2,1-f][1,2,4]triazin-5-yl]methyl]piperidin-3-ol of the formula

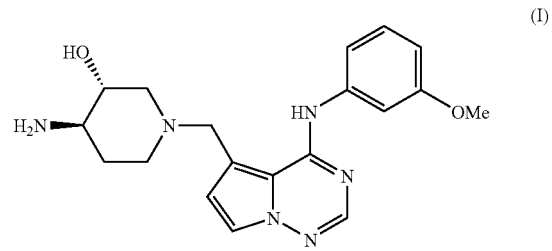

(I)

are provided. Also provided is a pharmaceutical composition comprising one or more crystalline forms of (3R,4R)-4-amino-1-[[4-[(3-methoxyphenyl)amino]pyrrolo[2,1-f][1,2,4]triazin-5-yl]methyl]piperidin-3-ol, as well as a method of using one or more crystalline forms of (3R,4R)-4-amino-1-[[4-[(3-methoxyphenyl)amino]pyrrolo[2,1-f][1,2,4]triazin-5-yl]methyl]piperidin-3-ol in the treatment of cancer and other proliferative diseases.

22 Claims, 9 Drawing Sheets

N-2 FB pXRD

N-1 FB pXRD

N-1 HCl pXRD

DSC for N-2 Free Base

DSC for N-1 Free Base

DSC for N-1 HCl Salt

TGA for N-2 FB

TGA for N-1 Free Base

TGA for N-1 HCl salt

CRYSTALLINE FORMS OF (3R,4R)-4-AMINO-1-[[4-[(3-METHOXYPHENYL)AMINO]PYRROLO[2,1-F][1,2,4]TRIAZIN-5-YL]METHYL]PIPERIDIN-3-OL

This application claims priority benefit under Title 35 § 119(e) of U.S. Provisional Application No. 60/773,923, filed on Feb. 16, 2006, incorporated herein by reference in its entirety.

FIELD OF THE INVENTION

The present invention generally relates to crystalline forms of (3R,4R)-4-amino-1-[[4-[(3-methoxyphenyl)amino]pyrrolo[2,1-f][1,2,4]triazin-5-yl]methyl]piperidin-3-ol. The present invention also relates to a pharmaceutical composition comprising a crystalline form of (3R,4R)-4-amino-1-[[4-[(3-methoxyphenyl)amino]pyrrolo[2,1-f][1,2,4]triazin-5-yl]methyl]piperidin-3-ol, as well as a method of using a crystalline form of (3R,4R)-4-amino-1-[[4-[(3-methoxyphenyl)amino]pyrrolo[2,1-f][1,2,4]triazin-5-yl]methyl]piperidin-3-ol in the treatment of cancer and other proliferative diseases.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal-growth-factor receptor (HER) family consists of four distinct polypeptides, each with a cytoplasmic sequence homologous to other protein tyrosine kinases. Surveys have shown that HER1 and HER2 are over expressed in many tumor types. HER1 has been shown to be over expressed in the majority of solid tumors, and can be activated by either autocrine expression of ligand(s) or paracrine ligand expression by stromal elements. HER1 expression has been demonstrated in as much as 80-90% of colon and non-small cell lung cancer (NSCLC). HER2 gene amplification and over expression of the protein have been shown to occur in about 30% of all breast cancer. Clinical studies have shown unequivocally that HER2 gene amplification is a prognostic indicator for poor outcome in breast cancer. In addition to breast cancer, there is a good correlation between HER2 gene amplification and over expression in gastric, salivary gland, and bladder cancer. Co-expression of HER1 and HER2 has been demonstrated in breast, ovarian, bladder, and gastric tumors, as well as squamous cell carcinoma of the head and neck (SCCHN). Since HER1 and HER2 form heterodimers that are activated by EGF and related ligands, heterodimer signaling is believed to play a significant role in the pathobiology of these tumors as well as in their resistance to agents targeting only one of the receptors. Receptor coexpression in tumor cells suggests that targeting both HER1 and HER2 will be more effective in modulating proliferation than inhibiting either receptor alone. Herceptin®, which targets HER2 over-expressing cells, has no effect on HER2/HER1 heterodimerization.

Vascular endothelial growth factor (VEGF) is a mitogenic growth factor that is required for tumor angiogenesis and signals through the VEGF receptor 2 (VEGFR2) on endothelial cells. Inhibition of VEGF signaling has been shown to be a clinically proven approach for treating solid tumors, most notably colon and NSCLC. The epidemiology of HER1 and HER2 expression in tumors (both homo-and heterodimers), together with the expression of VEGFR2 in the vasculature that support tumor growth, suggest that a molecule that targets these three signal transduction pathways in both tumor and endothelial cells will result in greater efficacy than inhibiting individual pathways alone.

(3R,4R)-4-amino-1-[[4-[(3-methoxyphenyl)amino]pyrrolo[2,1-f][1,2,4]triazin-5-yl]methyl]piperidin-3-ol is a potent inhibitor of HER1, HER2, HER4, and VEGFR2, which has demonstrated broad antiproliferative activity in various tumor cell lines and excellent anti-tumor efficacy in HER2 and HER1 driven tumor xenograft models.

(3R,4R)-4-amino-1-[[4-[(3-methoxyphenyl)amino]pyrrolo[2,1-f][1,2,4]triazin-5-yl]methyl]piperidin-3-ol, has the structure of formula I:

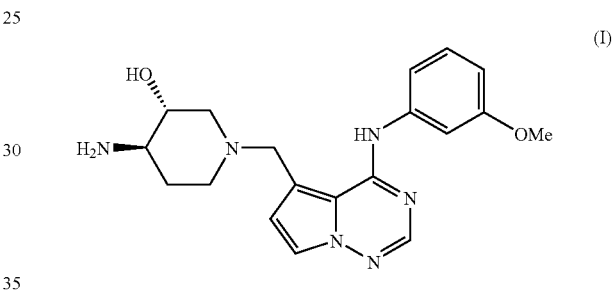

(I)

and is referred to herein as "Compound I". Compound I inhibits the tyrosine kinase activity of growth factor receptors such as HER1, HER2, and HER4 thereby making it useful as an anti-cancer agent. Compound I is disclosed in US 20050182058A1, published Aug. 18, 2005, which is assigned to the present assignee and is incorporated herein by reference in its entirety.

Typically, in the preparation of a pharmaceutical composition, a form of the active ingredient is sought that has a balance of desired properties such as dissolution rate, solubility, bioavailability, and/or storage stability. For example, it is desired that a form of the active ingredient, which has the requisite solubility and bioavailability, also has sufficient stability that it does not convert during manufacture or storage of the pharmaceutical composition to a different form, which has different solubility and/or bioavailability. One or more forms of Compound I are desired having properties and stability that allow the preparation of pharmaceutical compositions suitable for the treatment of diseases such as cancer. Further, one or more forms of Compound I are desired that allow the isolation and/or purification of Compound I, for example, during a preparative process.

It has been found through extensive testing of the various forms isolated that Form N-2 is more thermodynamically stable than Form N-1 at temperatures from room temperature to 50° C. Form N-1 melts at about 137° C. and recrystallizes as Form N-2, which then melts at about 150° C. Additionally, slurried mixtures of N-1 and N-2 convert to Form N-2 indicating it is monotropically more stable.

SUMMARY OF THE INVENTION

A first aspect of the present invention provides a crystalline form of Compound I:

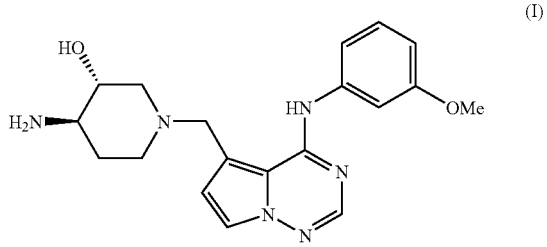

(I)

comprising Form N-2.

A second aspect of the present invention provides a crystalline form of Compound I comprising Form N-1.

A third aspect of the present invention provides a crystalline form of the hydrochloric acid salt of Compound I comprising Form N-1.

A further aspect of the invention provides a pharmaceutical composition comprising one or more of Form N-2, Form N-1, and/or the hydrochloric acid salt of Form N-1 of Compound I, and a pharmaceutically acceptable carrier or diluent.

Another aspect of the present invention provides a method for treating cancer, comprising administering to a mammalian species in need thereof, a therapeutically effect amount of Compound I, wherein Compound I is provided in a crystalline form comprising Form N-2, Form N-1, and/or the hydrochloric acid salt of Form N-1.

The names used herein to characterize a specific form, e.g. "N-1" etc., should not be considered limiting with respect to any other substance possessing similar or identical physical and chemical characteristics, but rather it should be understood that these designations are mere identifiers that should be interpreted according to the characterization information also presented herein.

BRIEF DESCRIPTION OF THE DRAWINGS

The invention is illustrated by reference to the accompanying drawings described below.

DETAILED DESCRIPTION OF THE INVENTION

Figure 1:
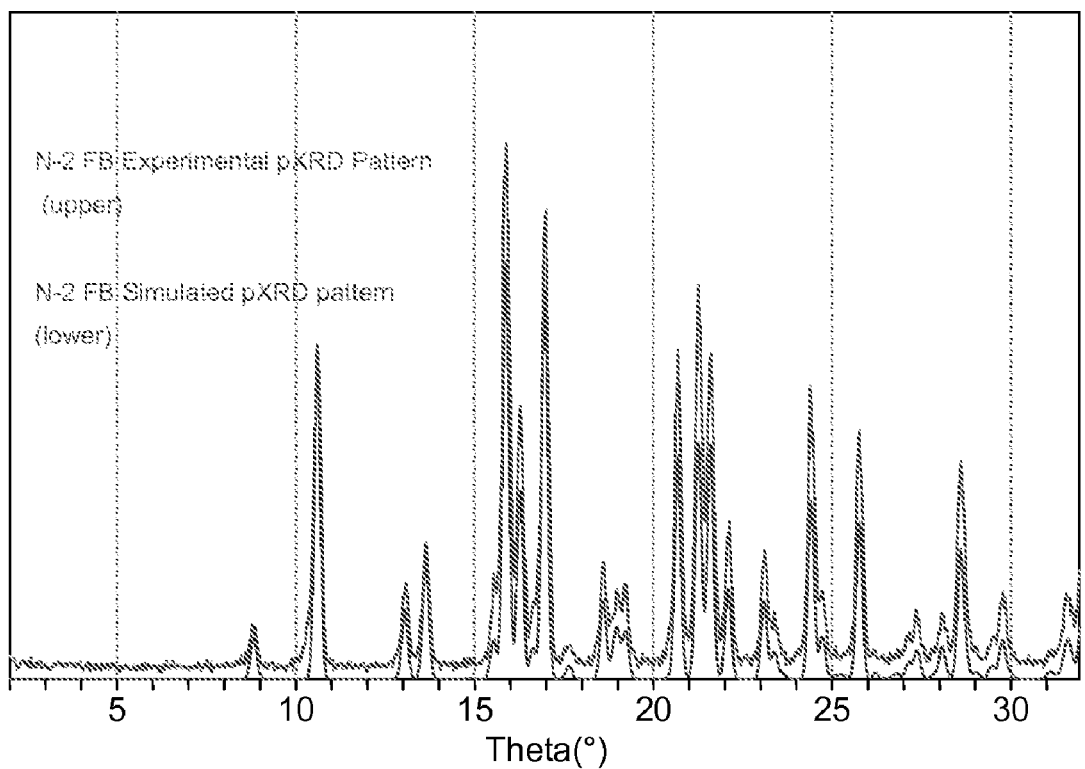
FIG. 1 shows observed (at room temperature) and simulated (at T=25°) powder x-ray diffraction patterns (CuKα λ=1.5418 Å) of the N-2 crystalline form of (3R,4R)-4-amino-1-[[4-[(3-methoxyphenyl)amino]pyrrolo[2,1-f][1,2,4]triazin-5-yl]methyl]piperidin-3-ol.

As used herein, "polymorphs" refer to crystalline forms having the same chemical compositions but different spatial arrangements of the molecules and/or ions forming the crystals.

As used herein, "amorphous" refers to a solid form of a molecule and/or ions that is not crystalline. An amorphous solid does not display a definitive X-ray diffraction pattern with sharp maxima.

As used herein, "substantially pure," when used in reference to a crystalline form, means a sample of the crystalline form of the compound having a purity greater than 90 weight %, including greater than 90, 91, 92, 93, 94, 95, 96, 97, 98, and 99 weight %, and also including equal to about 100 weight % of the compound, based on the weight of the compound. The remaining material comprises other form(s) of the compound, and/or reaction impurities and/or processing impurities arising from its preparation. For example, a crystalline form of Compound I may be deemed substantially pure in that it has a purity greater than 90 weight % of the crystalline form of Compound I, as measured by means that are at this time known and generally accepted in the art, where the remaining less than 10 weight % of material comprises other form(s) of Compound I and/or reaction impurities and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

As used herein, the parameter "molecules/asymmetric unit" refers to the number of molecules of Compound I in the asymmetric unit.

As used herein, the unit cell parameter "molecules/unit cell" refers to the number of molecules of Compound I in the unit cell.

When dissolved, the crystalline form of Compound I loses its crystalline structure, and is therefore referred to as a solution of Compound I. One or more of the crystalline forms of Compound I disclosed herein, may be used for the preparation of liquid formulations in which the compound is dissolved or suspended.

A therapeutically effective amount of the crystalline Form N-2, Form N-1, and/or the hydrochloric acid salt of crystalline Form N-1 of Compound I may be combined with a pharmaceutically acceptable carrier or diluent to provide pharmaceutical compositions of this invention. By "therapeutically effective amount", it is meant an amount that, when administered alone or an amount when administered with an additional therapeutic agent, is effective to prevent, suppress, or ameliorate a disease or condition or the progression of a disease or condition.

The present invention provides crystalline forms of Compound I,

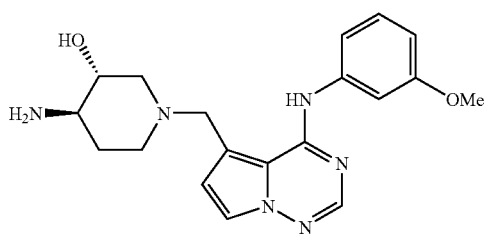

(I)

The first aspect of the invention provides a neat crystalline form of Compound I and is referred herein as the "Form N-2" or "N-2 Form".

In one embodiment, the N-2 Form of Compound I is characterized by unit cell parameters approximately equal to the following:

Cell dimensions: a=6.72 Å b=10.93 Å c=26.12 Å

α=90.0°

β=90.0

γ=90.0°

Space group: $P2_12_12_1$

Molecules of Compound I/asymmetric unit: 1

Volume=1917.7 Å$^3$

Density (calculated)=1.276 g/cm$^3$ wherein measurement of the crystalline form is at a temperature of about 25° C.

In a different embodiment, the N-2 Form of Compound I is characterized by the simulated powder x-ray diffraction pattern substantially in accordance with that shown in FIG. 1 and/or by the observed powder x-ray diffraction pattern substantially in accordance with that shown in FIG. 1.

In another embodiment, the N-2 Form of Compound I is characterized by a powder x-ray diffraction pattern (CuKα λ=1.5418 Å at a temperature of about 25° C.) comprising four or more 2θ values, preferably comprising five or more 2θ values, selected from: 10.5±0.1, 13.0±0.1, 13.6±0.1, 15.8±0.1, 16.2±0.1, 16.9±0.1, 20.6±0.1, 21.2±0.1, 21.5±0.1, 24.4±0.1, 28.6±0.1, wherein measurement of the crystalline form is at a temperature of about 25° C. Characteristic diffraction peak positions (degrees 2θ±0.1) @RT are based on a high quality pattern collected with a diffractometer (CuKα) with a spinning capillary and 2θ calibrated with a NIST (National Institute of Standards and Technology) or other suitable standard.

In a further embodiment, the N-2 Form of Compound I is characterized by fractional atomic coordinates substantially as listed in Table 1.

TABLE 1

Fractional Atomic Coordinates for Form N-2 at T = 25° C.

| Atom | X | Y | Z |
|---|---|---|---|
| O1 | −0.2270 | 0.7789 | 0.0491 |
| C2 | 0.3033 | 0.3612 | 0.1113 |
| O3 | 0.4931 | 0.0950 | 0.0465 |
| N4 | −0.0440 | 0.2203 | 0.1493 |
| N5 | 0.1430 | 0.4019 | 0.1422 |
| C6 | 0.4478 | 0.4483 | 0.1008 |
| C7 | −0.0544 | 0.7407 | 0.0766 |
| N8 | 0.0484 | 0.6586 | 0.1605 |
| N9 | −0.3212 | 0.3379 | 0.2065 |
| N10 | 0.1537 | 0.8851 | 0.0298 |
| C11 | −0.0155 | 0.3380 | 0.1602 |
| C12 | 0.4885 | 0.2151 | 0.0631 |
| N13 | −0.3579 | 0.2183 | 0.1940 |
| C14 | −0.1501 | 0.4018 | 0.1924 |
| C15 | 0.6100 | 0.4177 | 0.0707 |
| C16 | −0.1659 | 0.5185 | 0.2129 |
| C17 | 0.6313 | 0.3002 | 0.0514 |
| C18 | −0.1232 | 0.7025 | 0.1304 |
| C19 | 0.2003 | 0.7546 | 0.1655 |
| C20 | 0.0950 | 0.8440 | 0.0812 |
| C21 | 0.3216 | 0.2420 | 0.0929 |
| C22 | −0.0166 | 0.6209 | 0.2128 |
| C23 | −0.2138 | 0.1694 | 0.1674 |
| C24 | 0.2709 | 0.7985 | 0.1127 |
| C25 | −0.4411 | 0.4123 | 0.2352 |
| C26 | −0.3517 | 0.5241 | 0.2397 |
| C27 | 0.6581 | 0.0566 | 0.0176 |
| H28 | −0.1718 | 0.8496 | 0.0227 |
| H29 | 0.1482 | 0.5009 | 0.1533 |
| H30 | 0.4288 | 0.5419 | 0.1158 |
| H31 | 0.0195 | 0.6642 | 0.0581 |
| H32 | 0.2785 | 0.9486 | 0.0318 |
| H33 | 0.2049 | 0.8053 | 0.0072 |
| H34 | 0.7190 | 0.4890 | 0.0629 |
| H35 | 0.7621 | 0.2765 | 0.0273 |
| H36 | −0.1941 | 0.7804 | 0.1493 |
| H37 | −0.2354 | 0.6305 | 0.1267 |
| H38 | 0.1392 | 0.8325 | 0.1861 |
| H39 | 0.3285 | 0.7208 | 0.1871 |
| H40 | 0.0207 | 0.9203 | 0.1012 |
| H41 | 0.2100 | 0.1687 | 0.1024 |
| H42 | 0.1131 | 0.5960 | 0.2353 |
| H43 | −0.0823 | 0.7033 | 0.2311 |
| H44 | −0.2318 | 0.0705 | 0.1591 |
| H45 | 0.3803 | 0.8729 | 0.1177 |
| H46 | 0.3452 | 0.7241 | 0.0932 |
| H47 | −0.5838 | 0.3822 | 0.2539 |
| H48 | −0.4147 | 0.6070 | 0.2592 |
| H49 | 0.6475 | −0.0392 | 0.0068 |
| H50 | 0.6820 | 0.1114 | −0.0158 |
| H51 | 0.7958 | 0.0644 | 0.0418 |
| — | — | — | — |
| — | — | — | — |

Figure 4:
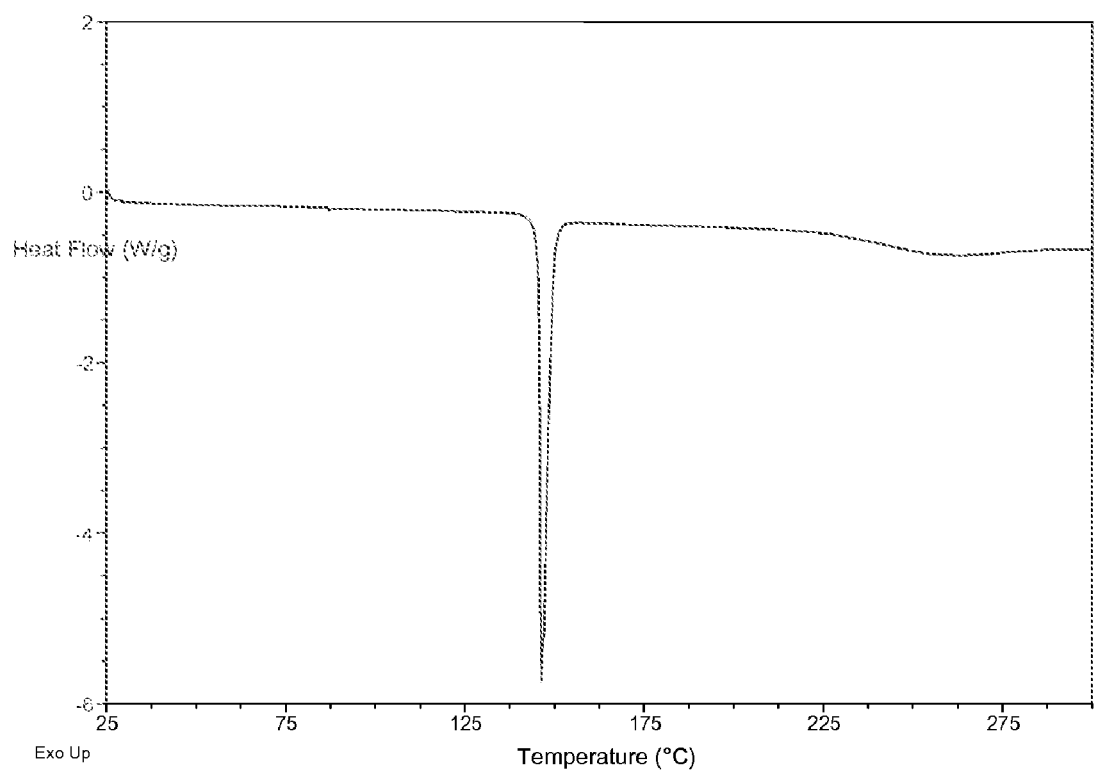
FIG. 4 shows a differential scanning calorimetry thermogram of the N-2 crystalline form of (3R,4R)-4-amino-1-[[4-[(3-methoxyphenyl)amino]pyrrolo[2,1-f][1,2,4]triazin-5-yl]methyl]piperidin-3-ol.

In a still further embodiment, the N-2 Form of Compound I is characterized by a differential scanning calorimetry thermogram substantially in accordance with that shown in FIG. 4. The N-2 Form may be characterized by a melting point in the range of from about 145° C. to about 149° C.

Figure 7:
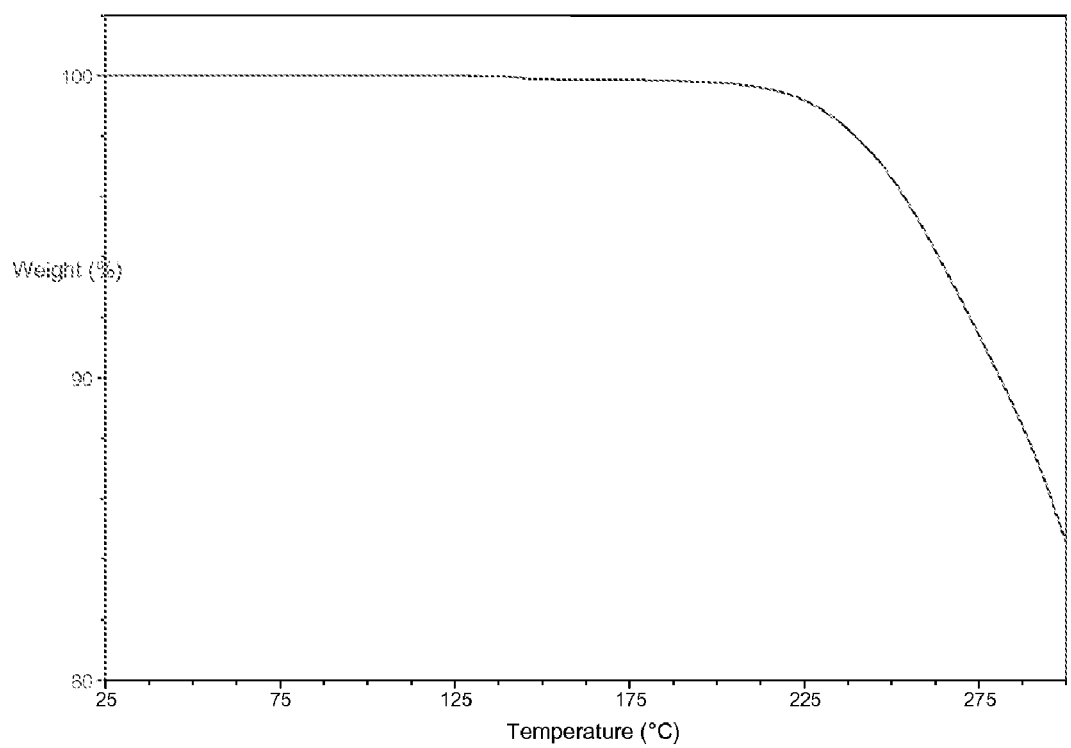
FIG. 7 shows a thermogravimetric analysis (TGA) thermogram of the N-2 crystalline form of (3R,4R)-4-amino-1-[[4-[(3-methoxyphenyl)amino]pyrrolo[2,1-f][1,2,4]triazin-5-yl]methyl]piperidin-3-ol.

In another embodiment, the N-2 Form of Compound I is characterized by a thermogravimetric analysis (TGA) thermogram having negligible weight loss upon heating to a temperature of about 150° C. The invention also provides the N-2 Form of Compound I that exhibits a TGA thermogram substantially the same as shown in FIG. 7.

In still another embodiment, the N-2 Form is provided in substantially pure form. This N-2 Form of Compound I in substantially pure form may be employed in pharmaceutical compositions which may optionally include one or more other components selected, for example, from excipients and carriers; and optionally, one or more other active pharmaceutical ingredients having active chemical entities of different molecular structures.

Preferably, the N-2 form has substantially pure phase homogeneity as indicated by less than 10%, preferably less than 5%, and more preferably less than 2% of the total peak area in the experimentally measured powder x-ray diffraction (PXRD) pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

For example, the N-2 Form may be provided in substantially pure form, wherein substantially pure is greater than 90 weight % pure, preferably greater than 95 weight % pure, and more preferably greater than 99 weight % pure.

In a different embodiment, a composition is provided consisting essentially of Form N-2 of Compound I. The composition of this embodiment may comprise at least 90 weight %, preferably at least 95 weight %, and more preferably at least 99 weight % of the Form N-2 of Compound I, based on the weight of Compound I in the composition.

The second aspect of the invention provides a neat crystalline form of Compound I and is referred herein as the "Form N-1" or "N-1 Form".

In one embodiment, the N-1 Form of Compound I is characterized by unit cell parameters approximately equal to the following:

Cell dimensions: a=6.72 Å b=14.06 Å c=19.93 Å

α=90.0°

β=90.0°

γ=90.0°

Space group: $P2_12_12_1$

Molecules of Compound I/asymmetric unit: 1

Volume=1882.1 Å$^3$

Density (calculated)=1.300 g/cm$^3$ wherein measurement of said crystalline form is at a temperature of about 25° C.

Figure 2:
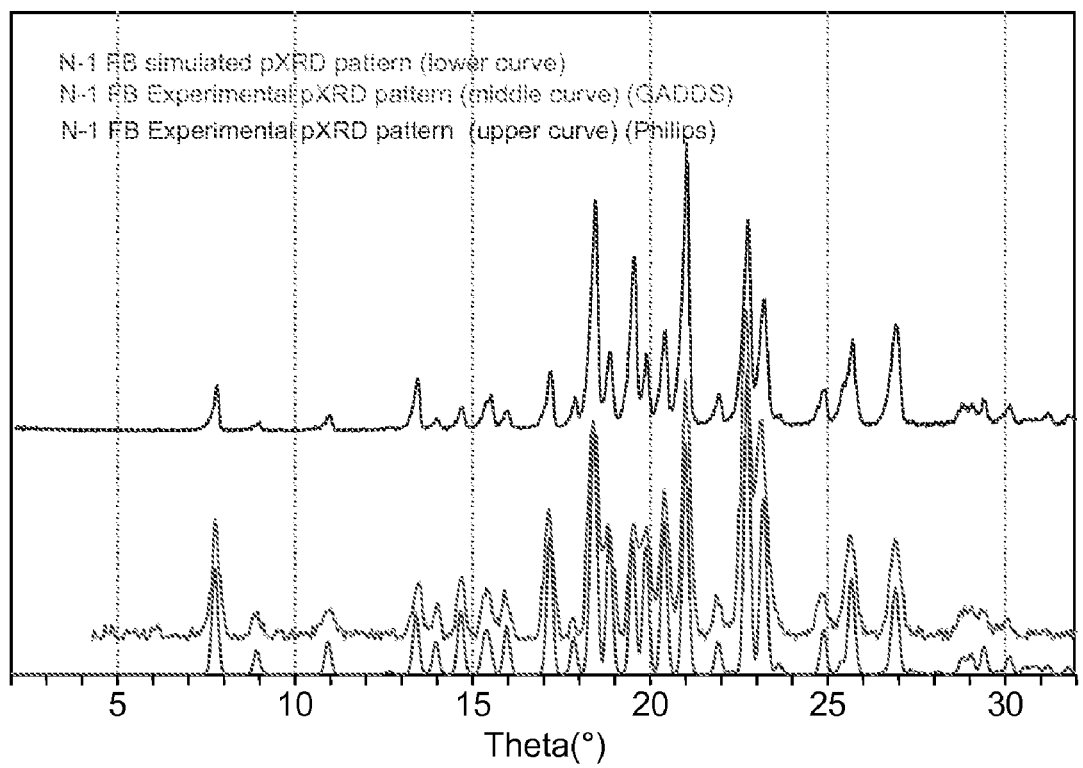
FIG. 2 shows observed (at room temperature) and simulated (at T=25°) powder x-ray diffraction patterns (CuKα λ=1.5418 Å) of the N-1 crystalline form of (3R,4R)-4-amino-1-[[4-[(3-methoxyphenyl)amino]pyrrolo[2,1-f][1,2,4]triazin-5-yl]methyl]piperidin-3-ol.

In a different embodiment, the N-1 Form of Compound I is characterized by the simulated powder x-ray diffraction pattern substantially in accordance with that shown in FIG. 2 and/or by the observed powder x-ray diffraction pattern substantially in accordance with that shown in FIG. 2.

In another embodiment, the N-1 Form of Compound I is characterized by a powder x-ray diffraction pattern (CuKα λ=1.5418 Å at a temperature of about 25° C.) comprising four or more 2θ values, preferably comprising five or more 2θ values, (CuKα λ=1.5418 Å) selected from: 7.7±0.1, 13.4±0.1, 14.6±0.1, 19.5±0.1 19.8±0.1 20.3±0.1 20.9±0.1, 22.7±0.1, 26.9±0.1, wherein measurement of the crystalline form is at a temperature of about 25° C. Characteristic diffraction peak positions (degrees 2θ±0.1) @RT are based on a high quality pattern collected with a diffractometer (CuKα) with a spinning capillary and 2θ calibrated with a NIST or other suitable standard.

In a further embodiment, the N-1 Form of Compound I is characterized by fractional atomic coordinates substantially as listed in Table 2.

TABLE 2

Fractional Atomic Coordinates for Form N-1 at T = 25° C.

| Atom | X | Y | Z |
| --- | --- | --- | --- |
| O1 | −0.0268 | 0.2930 | 0.0722 |
| O2 | 0.1229 | −0.0389 | 0.0070 |
| C3 | 0.3013 | 0.3551 | 0.0667 |
| C4 | 0.1942 | 0.2586 | 0.1646 |
| C5 | 0.3091 | −0.0527 | 0.0329 |
| N6 | 0.2952 | 0.3654 | −0.0072 |
| C7 | 0.5395 | −0.0066 | 0.1207 |
| N8 | 0.4026 | 0.2426 | 0.1847 |
| N9 | 0.9054 | 0.1352 | 0.3045 |
| N10 | 0.5736 | 0.0560 | 0.1736 |
| C11 | 0.5297 | 0.3234 | 0.1633 |
| C12 | 0.6166 | 0.2086 | 0.2844 |
| C13 | 0.7337 | 0.1309 | 0.2662 |
| C14 | 0.5192 | 0.3358 | 0.0893 |
| C15 | 0.3529 | 0.0021 | 0.0893 |
| C16 | 0.1735 | 0.2720 | 0.0885 |
| C17 | 0.7284 | 0.0557 | 0.2174 |
| C18 | 0.4429 | −0.1182 | 0.0066 |
| N19 | 1.0548 | 0.0674 | 0.3037 |
| N20 | 0.8695 | −0.0112 | 0.2175 |
| C21 | 0.4096 | 0.2332 | 0.2600 |
| C22 | 0.6801 | −0.0728 | 0.0963 |
| C23 | 0.7229 | 0.2601 | 0.3325 |
| C24 | 0.6268 | −0.1259 | 0.0391 |
| C25 | 0.0753 | −0.0886 | −0.0553 |
| C26 | 0.9009 | 0.2137 | 0.3442 |
| C27 | 1.0199 | −0.0010 | 0.2612 |
| H28 | −0.0948 | 0.2318 | 0.0478 |
| H29 | 0.2541 | 0.4237 | 0.0902 |
| H30 | 0.0992 | 0.2017 | 0.1823 |
| H31 | 0.1391 | 0.3253 | 0.1889 |
| H32 | 0.1440 | 0.3847 | −0.0231 |
| H33 | 0.3946 | 0.4222 | −0.0240 |
| H34 | 0.4622 | 0.1121 | 0.1804 |
| H35 | 0.4799 | 0.3885 | 0.1875 |
| H36 | 0.6838 | 0.3107 | 0.1779 |
| H37 | 0.5678 | 0.2712 | 0.0638 |
| H38 | 0.6147 | 0.3940 | 0.0725 |
| H39 | 0.2452 | 0.0552 | 0.1081 |
| H40 | 0.2207 | 0.2075 | 0.0610 |
| H41 | 0.4000 | −0.1604 | −0.0390 |
| H42 | 0.3606 | 0.2991 | 0.2825 |
| H43 | 0.3050 | 0.1770 | 0.2747 |
| H44 | 0.8272 | −0.0810 | 0.1203 |
| H45 | 0.6750 | 0.3267 | 0.3575 |
| H46 | 0.7367 | −0.1749 | 0.0185 |
| H47 | −0.0759 | −0.0701 | −0.0708 |
| H48 | 0.1762 | −0.0671 | −0.0954 |
| H49 | 0.0850 | −0.1640 | −0.0484 |
| H50 | 1.0161 | 0.2346 | 0.3791 |
| H51 | 1.1282 | −0.0612 | 0.2610 |
| — | — | — | — |
| — | — | — | — |

Figure 5:
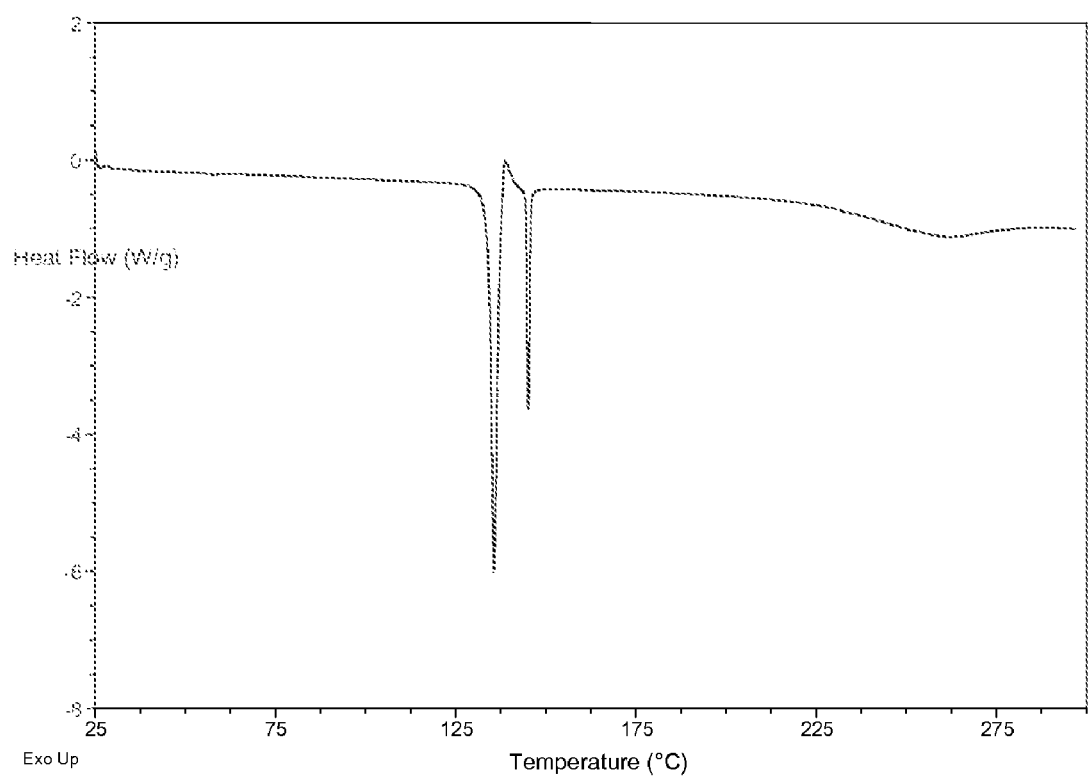
FIG. 5 shows a differential scanning calorimetry thermogram of the N-1 crystalline form of (3R,4R)-4-amino-1-[[4-[(3-methoxyphenyl)amino]pyrrolo[2,1-f][1,2,4]triazin-5-yl]methyl]piperidin-3-ol.

In a still further embodiment, the N-1 Form of Compound I is characterized by a differential scanning calorimetry thermogram substantially in accordance with that shown in FIG. 5. The N-1 Form may be characterized by a melting point in the range of from about 134° C. to about 140° C.

Figure 8:
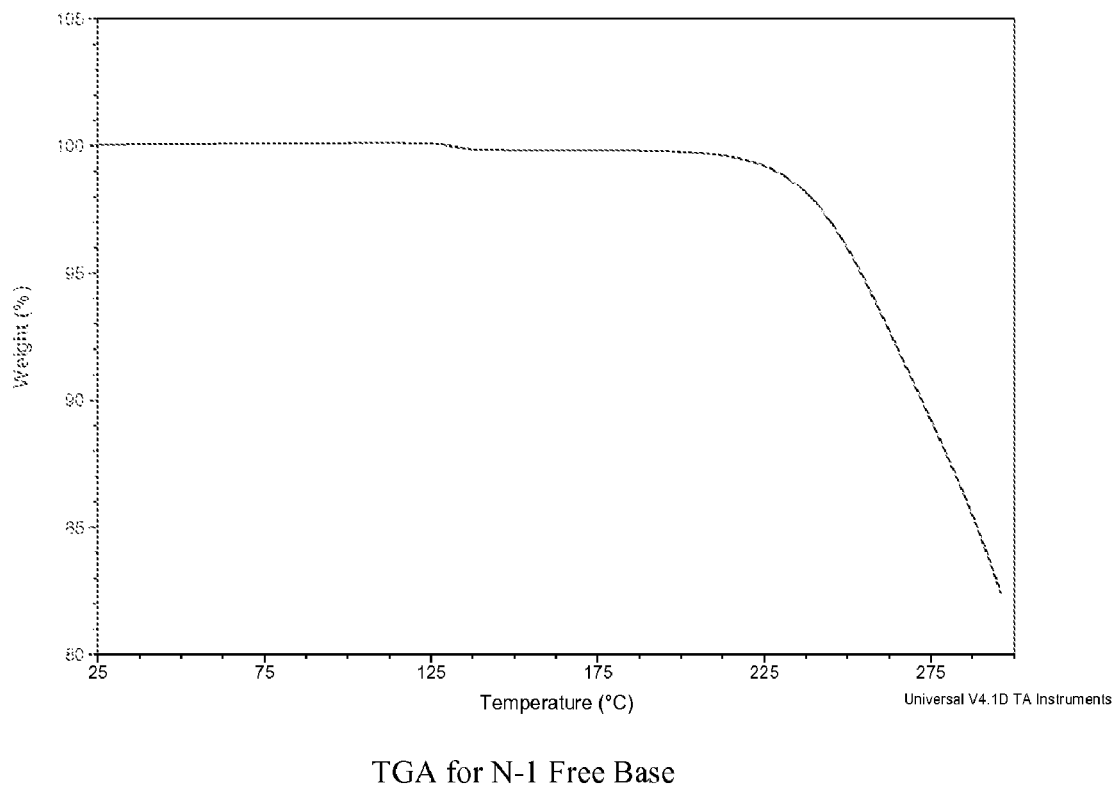
FIG. 8 shows a thermogravimetric analysis (TGA) thermogram of the N-1 crystalline form of (3R,4R)-4-amino-1-[[4-[(3-methoxyphenyl)amino]pyrrolo[2,1-f][1,2,4]triazin-5-yl]methyl]piperidin-3-ol.

In another embodiment, the N-1 Form of Compound I is characterized by a thermogravimetric analysis (TGA) thermogram having minimal weight loss upon heating to a temperature of about 150° C. The invention also provides the N-1 Form of Compound I that exhibits a TGA thermogram substantially the same as shown in FIG. 8.

In still another embodiment, the N-1 Form is provided in substantially pure form. This N-1 Form of Compound I in substantially pure form may be employed in pharmaceutical compositions which may optionally include one or more other components selected, for example, from excipients and carriers; and optionally, one or more other active pharmaceutical ingredients having active chemical entities of different molecular structures.

Preferably, the N-1 form has substantially pure phase homogeneity as indicated by less than 10%, preferably less than 5%, and more preferably less than 2% of the total peak area in the experimentally measured powder x-ray diffraction (PXRD) pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

For example, the N-1 Form may be provided in substantially pure form, wherein substantially pure is greater than 90 weight % pure, preferably greater than 95 weight % pure, and more preferably greater than 99 weight % pure.

In a different embodiment, a composition is provided consisting essentially of the Form N-1 of Compound I. The composition of this embodiment may comprise at least 90 weight %, preferably at least 95 weight %, and more preferably at least 99 weight % of the Form N-1 of Compound I, based on the weight of Compound I in the composition.

The third aspect of the invention provides a hydrochloric acid salt crystalline form of Compound I and is referred herein as the "HCl salt of Form N-1" or "N-1 Form HCl salt".

In one embodiment, the HCl salt of Form N-1 of Compound I is characterized by unit cell parameters approximately equal to the following:

Cell dimensions: a=33.67 Å b=7.18 Å c=23.51 Å

α=90.0°

β=132.4°

γ=90.0°

Space group: C2

Molecules of Compound I/asymmetric unit: 2

Volume=4199.4 Å$^3$

Density (calculated)=1.281 g/cm$^3$ wherein measurement of said crystalline form is at a temperature of about 25° C.

Figure 3:
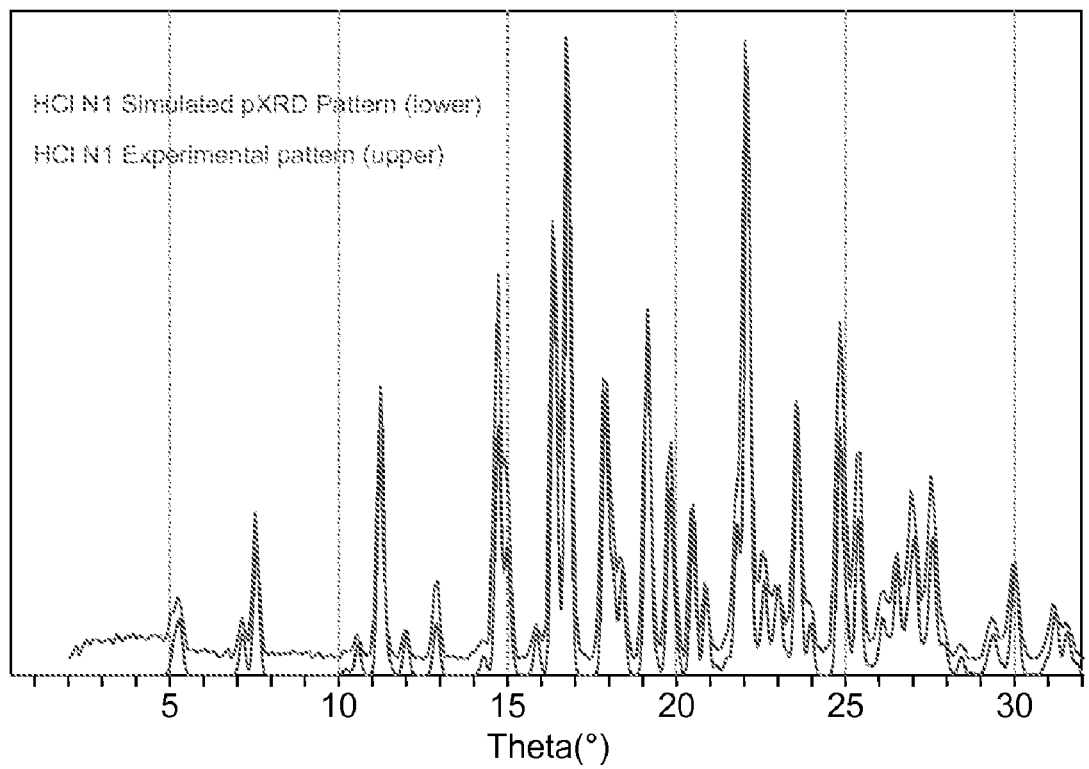
FIG. 3 shows observed (at room temperature) and simulated (at T=25°) powder x-ray diffraction patterns (CuKα λ=1.5418 Å) of the hydrochloric acid salt of the N-1 crystalline form of (3R,4R)-4-amino-1-[[4-[(3-methoxyphenyl)amino]pyrrolo[2,1-f][1,2,4]triazin-5-yl]methyl]piperidin-3-ol.

In a different embodiment, the HCl salt of Form N-1of Compound I is characterized by the simulated powder x-ray diffraction pattern substantially in accordance with that shown in FIG. 3 and/or by the observed powder x-ray diffraction pattern substantially in accordance with that shown in FIG. 3.

In another embodiment, the HCl salt of Form N-1 of Compound I is characterized by a powder x-ray diffraction pattern (CuKα λ=1.5418 Å at a temperature of about 25° C.) comprising four or more 2θ values, preferably comprising five or more 2θ values, (CuKα λ=1.5418 Å) selected from: 5.2±0.1, 11.2±0.1, 16.3±0.1, 16.7±0.1, 19.1±0.1, 22.1±0.1, 23.5±0.1, 27.5±0.1, wherein measurement of said crystalline form is at a temperature of about 25° C. Characteristic diffraction peak positions (degrees 2θ±0.1) @RT are based on a high quality pattern collected with a diffractometer (CuKα) with a spinning capillary and 2θ calibrated with a NIST or other suitable standard.

In a further embodiment, the HCl salt of Form N-1 of Compound I is characterized by fractional atomic coordinates substantially as listed in Table 3.

TABLE 3

Fractional Atomic Coordinates for the HCl salt of Form N-1 at T = 25° C.

| Atom | X | Y | Z |
| --- | --- | --- | --- |
| O1 | 0.3861 | 0.5122 | 0.2579 |
| O2 | 0.3479 | −0.1270 | 0.1436 |
| N3 | 0.2004 | 0.0860 | 0.1084 |
| C4 | 0.2178 | −0.0356 | 0.0811 |
| N5 | 0.4247 | 0.2998 | 0.3904 |
| N6 | 0.2573 | 0.4067 | 0.2082 |
| C7 | 0.3320 | 0.2857 | 0.3382 |
| C8 | 0.3499 | 0.4140 | 0.2588 |
| N9 | 0.1240 | −0.0781 | 0.0642 |
| C10 | 0.1432 | 0.2252 | 0.1216 |
| C11 | 0.1551 | 0.0722 | 0.0973 |
| N12 | 0.0998 | 0.1951 | 0.1166 |
| C13 | 0.1623 | 0.4015 | 0.1501 |
| C14 | 0.3714 | 0.3956 | 0.3397 |
| C15 | 0.2954 | 0.5108 | 0.2090 |
| C16 | 0.2597 | −0.2473 | 0.0322 |
| C17 | 0.2728 | −0.0366 | 0.1236 |
| C18 | 0.2928 | −0.1410 | 0.0981 |
| N19 | 0.0676 | 0.0410 | 0.0855 |
| C20 | 0.2050 | 0.5056 | 0.1591 |
| C21 | 0.1833 | −0.1407 | 0.0146 |
| C22 | 0.2784 | 0.3876 | 0.2866 |
| C23 | 0.0928 | 0.3505 | 0.1421 |
| C24 | 0.3721 | −0.2414 | 0.1250 |
| C25 | 0.2044 | −0.2440 | −0.0088 |
| C26 | 0.1309 | 0.4803 | 0.1634 |
| C27 | 0.0810 | −0.0796 | 0.0601 |
| N28 | 0.4557 | 0.7890 | 0.5290 |
| C29 | 0.3177 | 0.6885 | 0.6550 |
| N30 | 0.2658 | 0.6501 | 0.6252 |
| O31 | 0.3430 | 0.7486 | 0.4408 |
| N32 | 0.4039 | 0.5646 | 0.7197 |
| C33 | 0.3559 | 0.5405 | 0.6990 |
| O34 | 0.5110 | 0.0845 | 0.9064 |
| N35 | 0.3439 | 0.3877 | 0.7167 |
| C36 | 0.3525 | 0.8636 | 0.5470 |
| N37 | 0.3898 | 0.8832 | 0.6308 |
| C38 | 0.4279 | 0.8856 | 0.5514 |
| N39 | 0.2524 | 0.4902 | 0.6409 |
| C40 | 0.2327 | 0.7954 | 0.5822 |
| C41 | 0.5050 | 0.2052 | 0.8566 |
| C42 | 0.4595 | 0.3167 | 0.8160 |
| C43 | 0.3628 | 0.9771 | 0.6529 |
| C44 | 0.3163 | 0.8647 | 0.6308 |
| C45 | 0.2924 | 0.3750 | 0.6860 |
| C46 | 0.4491 | 0.4404 | 0.7636 |
| C47 | 0.4839 | 0.4565 | 0.7503 |
| C48 | 0.3793 | 0.7706 | 0.5224 |
| C49 | 0.4665 | 0.9113 | 0.6377 |
| C50 | 0.4364 | 0.9974 | 0.6587 |
| C51 | 0.5292 | 0.3455 | 0.7923 |
| C52 | 0.2629 | 0.9286 | 0.5845 |
| C53 | 0.5409 | 0.2186 | 0.8461 |
| C54 | 0.5548 | −0.0422 | 0.9492 |
| CL55 | 0.5807 | 0.8702 | 0.6336 |
| CL56 | 0.4603 | 0.3593 | 0.5517 |
| H57 | 0.3996 | 0.6348 | 0.2932 |
| H58 | 0.2268 | 0.2018 | 0.1433 |
| H59 | 0.4516 | 0.3640 | 0.3861 |
| H60 | 0.4437 | 0.3063 | 0.4509 |
| H61 | 0.4198 | 0.1538 | 0.3747 |
| H62 | 0.3272 | 0.1474 | 0.3165 |
| H63 | 0.3475 | 0.2743 | 0.3966 |
| H64 | 0.3444 | 0.2748 | 0.2357 |
| H65 | 0.3766 | 0.5340 | 0.3628 |
| H66 | 0.2786 | 0.5231 | 0.1505 |
| H67 | 0.3010 | 0.6497 | 0.2319 |
| H68 | 0.2758 | −0.3345 | 0.0139 |
| H69 | 0.2999 | 0.0455 | 0.1765 |
| H70 | 0.2111 | 0.6401 | 0.1844 |
| H71 | 0.1921 | 0.5238 | 0.1031 |
| H72 | 0.1410 | −0.1402 | −0.0171 |
| H73 | 0.2833 | 0.5224 | 0.3111 |
| H74 | 0.2497 | 0.3071 | 0.2844 |
| H75 | 0.0615 | 0.3699 | 0.1439 |

TABLE 3-continued

Fractional Atomic Coordinates for the HCl salt of Form N-1 at T = 25° C.

| Atom | X | Y | Z |
|------|--------|---------|---------|
| H76  | 0.4149 | −0.2209 | 0.1650  |
| H77  | 0.3650 | −0.3898 | 0.1303  |
| H78  | 0.3545 | −0.2188 | 0.0675  |
| H79  | 0.1767 | −0.3217 | −0.0625 |
| H80  | 0.1377 | 0.6218  | 0.1878  |
| H81  | 0.0536 | −0.2003 | 0.0289  |
| H82  | 0.4976 | 0.8286  | 0.5688  |
| H83  | 0.4526 | 0.6396  | 0.5309  |
| H84  | 0.4372 | 0.8292  | 0.4712  |
| H85  | 0.3091 | 0.8393  | 0.4147  |
| H86  | 0.4089 | 0.6940  | 0.7007  |
| H87  | 0.3172 | 0.7861  | 0.5262  |
| H88  | 0.3390 | 1.0035  | 0.5210  |
| H89  | 0.4133 | 1.0196  | 0.5229  |
| H90  | 0.1908 | 0.8022  | 0.5509  |
| H91  | 0.4318 | 0.3025  | 0.8253  |
| H92  | 0.3904 | 1.0075  | 0.7122  |
| H93  | 0.3459 | 1.1107  | 0.6201  |
| H94  | 0.2828 | 0.2488  | 0.7015  |
| H95  | 0.4748 | 0.5525  | 0.7053  |
| H96  | 0.3936 | 0.6312  | 0.5498  |
| H97  | 0.4827 | 0.7755  | 0.6663  |
| H98  | 0.5000 | 0.9983  | 0.6573  |
| H99  | 0.4216 | 1.1360  | 0.6320  |
| H100 | 0.4627 | 1.0154  | 0.7205  |
| H101 | 0.5568 | 0.3548  | 0.7831  |
| H102 | 0.2473 | 1.0633  | 0.5539  |
| H103 | 0.5774 | 0.1306  | 0.8796  |
| H104 | 0.5545 | −0.1290 | 0.9855  |
| H105 | 0.5528 | −0.1311 | 0.9089  |
| H106 | 0.5929 | 0.0335  | 0.9837  |

Figure 6:
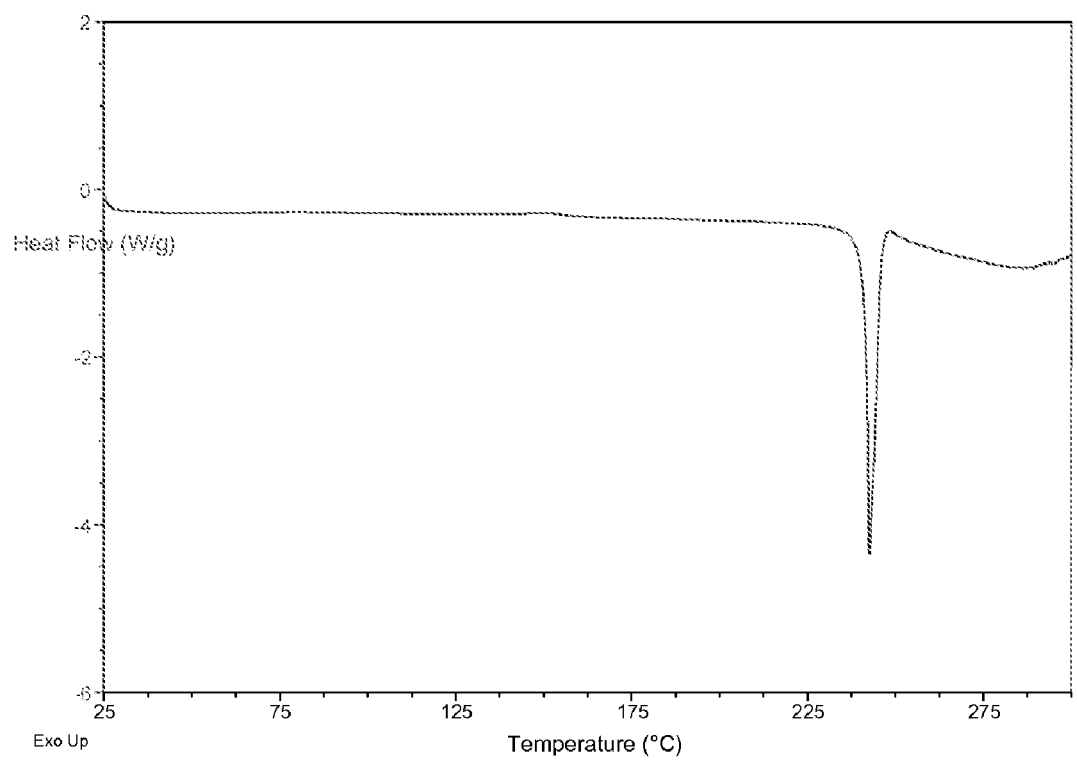
FIG. 6 shows a differential scanning calorimetry thermogram of the hydrochloric acid salt of the N-1 crystalline form of (3R,4R)-4-amino-1-[[4-[(3-methoxyphenyl)amino]pyrrolo[2,1-f][1,2,4]triazin-5-yl]methyl]piperidin-3-ol.

In a still further embodiment, the HCl salt of Form N-1 of Compound I is characterized by a differential scanning calorimetry thermogram substantially in accordance with that shown in FIG. 6. The HCl salt of Form N-1 may be characterized by a melting point in the range of from about 230° C. to about 245° C.

Figure 9:
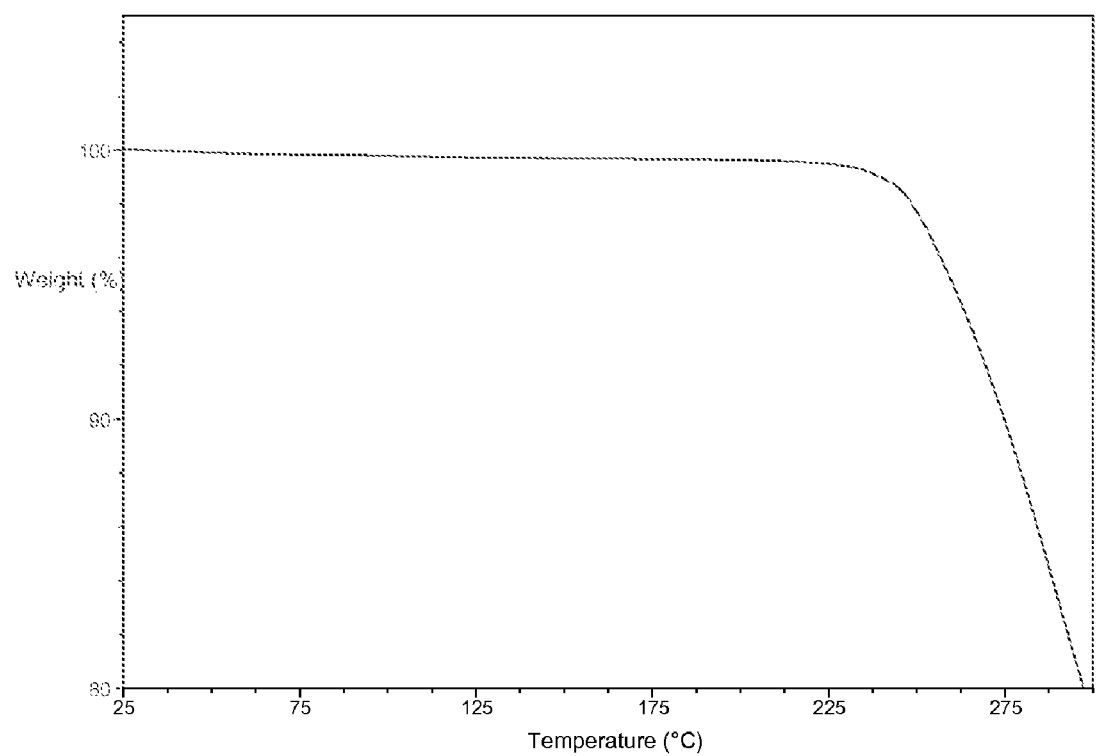
FIG. 9 shows a thermogravimetric analysis (TGA) thermogram of the hydrochloric acid salt of the N-1 crystalline form of (3R,4R)-4-amino-1-[[4-[(3-methoxyphenyl)amino]pyrrolo[2,1-f][1,2,4]triazin-5-yl]methyl]piperidin-3-ol.

In another embodiment, the HCl salt of Form N-1 of Compound I is characterized by a thermogravimetric analysis (TGA) thermogram having negligible weight loss upon heating to a temperature of about 150° C. The invention also provides the HCl salt of Form N-1 of Compound I that exhibits a TGA thermogram substantially the same as shown in FIG. 9.

In still another embodiment, the HCl salt of Form N-1 is provided in substantially pure form. This HCl salt of Form N-1 of Compound I in substantially pure form may be employed in pharmaceutical compositions which may optionally include one or more other components selected, for example, from excipients and carriers; and optionally, one or more other active pharmaceutical ingredients having active chemical entities of different molecular structures.

Preferably, the HCl salt of Form N-1 has substantially pure phase homogeneity as indicated by less than 10%, preferably less than 5%, and more preferably less than 2% of the total peak area in the experimentally measured powder x-ray diffraction (PXRD) pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

For example, the HCl salt of Form N-1 may be provided in substantially pure form, wherein substantially pure is greater than 90 weight % pure, preferably greater than 95 weight % pure, and more preferably greater than 99 weight % pure.

In a different embodiment, a composition is provided consisting essentially of the HCl salt of Form N-1 of Compound I. The composition of this embodiment may comprise at least 90 weight %, preferably at least 95 weight %, and more preferably at least 99 weight % of the HCl salt of Form N-1 of Compound I, based on the weight of Compound I in the composition.

The present invention also provides a pharmaceutical composition comprising a crystalline form of Compound I, wherein Compound I is in Form N-2; and a pharmaceutically acceptable carrier or diluent. The pharmaceutical composition may comprise the Form N-2 in substantially pure form.

The present invention also provides a pharmaceutical composition comprising a crystalline form of Compound I, wherein Compound I is in Form N-1; and pharmaceutically acceptable carrier or diluent. The pharmaceutical composition may comprise the Form N-1 in substantially pure form.

Further, the present invention provides a pharmaceutical composition comprising a crystalline form of Compound I, wherein Compound I is in the HCl salt of Form N-1; and pharmaceutically acceptable carrier or diluent. The pharmaceutical composition may comprise the HCl salt of Form N-1 in substantially pure form.

The present invention further provides a method for treating a proliferative disease, comprising administering to a mammalian species in need thereof, a therapeutically effective amount of Compound I, wherein Compound I is provided in a crystalline form comprising Form N-2, Form N-1, and/or the HCl salt of Form N-1. Preferably, the mammalian species is human. The method may comprise administering Compound I, wherein Compound I consists essentially of Form N-2. Alternatively, the method may comprise administering Compound I, wherein Compound I consists essentially of Form N-1. Also, the method may comprise administering Compound I, wherein Compound I consists essentially of the HCl salt of Form N-1.

Use and Utility

The present invention is based on the discovery that certain pyrrolotriazines are inhibitors of protein kinases. More specifically, pyrrolotriazines such as those described in this invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, oesophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of non-cancerous disorders such as psoriasis and rheumatoid arthritis.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit HER1, HER2, and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be over expressed in breast, ovarian, lung and gastric cancer. Monoclonal antibodies that downregulate the abundance of the HER2 receptor or inhibit signaling by the HER1 receptor have shown anti-tumor efficacy in preclinical and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agents such as Taxol®, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as anti-angiogenic agents. See the following documents and references cited therein: Schlessinger J., "Cell signaling by receptor tyrosine kinases", Cell 103(2), p. 211-225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", J. of Clin. Oncol. 17(9), p. 2639-2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", J. Clin. Oncol. 18(4), p. 904-914 (2000); Satoh, K., Kikuchi, S., Sekimata, M., Kabuyama, Y., Homma, M. K., and Homma Y., "Involvement of ErbB-2 in rheumatoid synovial cell growth", Arthritis Rheum. 44(2), p. 260-265 (2001).

The antiproliferative treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology, the other component(s) of such conjoint treatment in addition to the antiproliferative, antiangiogenic, and/or vascular permeability reducing treatment defined herein before may be: surgery, radiotherapy, or chemotherapy. Such chemotherapy may cover three main categories of therapeutic agent:

(i) antiangiogenic agents that work by different mechanisms from those defined hereinbefore (for example, linomide, inhibitors of integrin $\alpha v \beta 3$ function, angiostatin, and razoxane);

(ii) cytostatic agents such as antiestrogens (for example tamoxifen, toremifene, raloxifene, droloxifene, and iodoxifene), progestogens (for example megestrol acetate), aromatase inhibitors (for example anastrozole, letrozole, borazole, and exemestane), antihormones, antiprogestogens, antiandrogens (for example flutamide, nilutamide, bicalutamide, and cyproterone acetate), LHRH agonists and antagonists (for example gosereline acetate and leuprolide), inhibitors of testosterone $5\alpha$-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such as growth factor antibodies, growth factor receptor antibodies such as Avastin® (bevacizumab) and Erbitux® (cetuximab); tyrosine kinase inhibitors, and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); intercalating antitumor antibiotics (for example anthracyclines like doxorubicin, daunomycin, epirubicin, idarubicin, mitomycin-C, dactinomycin, and mithramycin); platinum derivatives (for example cisplatin and carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol® (paclitaxel), Taxotere® (docetaxel) and newer microbtubule agents such as epothilone analogs, discodermolide analogs, and eleutherobin analogs; topoisomerase inhibitors (for example epipodophyllotoxins like etoposide, teniposide, amsacrine, and topotecan); cell cycle inhibitors (for example flavopyridols); biological response modifiers, and proteasome inhibitors such as Velcade® (bortezomib).

As stated above, Compound I is of interest for its antiangiogenic and/or vascular permeability reducing effects. This compound is expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, Compound I is useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burkett's lymphoma;

hematopoietic tumors of myeloid lineage, including acute and chronic myelogenous leukemias, myelodysplastic syndrome, and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, seminoma, teratocarcinoma, osteosarcoma, xeroderma pigmentosum, keratoacanthoma, thyroid follicular cancer, and Kaposi's sarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

Compound I in one of the forms disclosed herein may be formulated with a pharmaceutical vehicle or diluent for oral, intravenous, or subcutaneous administration. The pharmaceutical composition can be formulated in a classical manner using solid or liquid vehicles, diluents, and/or additives appropriate to the desired mode of administration. Orally, one of the disclosed forms, such as Form N-2, Form N-1, and/or the HCl salt of Form N-1 of Compound I can be administered in the form of tablets, capsules, granules, powders, and the like. One or more of the crystalline forms of Compound I, such as Form N-2, Form N-1, and/or the HCl salt of Form N-1, may also be administered as a suspension using carriers appropriate to this mode of administration.

The effective amount of Compound I may be determined by one of ordinary skill in the art, and includes exemplary dosage amounts for a mammal of from about 0.05 to about 300 mg/kg/day, preferably less than about 200 mg/kg/day, in a single dose or in 2 to 4 divided doses. It will be understood that the specific dose level and frequency of dosage for any particular subject may be varied and will depend upon a variety of factors, the bioavailability of Compound I in the administered form, the metabolic stability and length of action of Compound I, the species, age, body weight, general health, sex, and diet of the subject, the mode and time of administration, rate of excretion, drug combination, and severity of the particular condition. Preferred subjects for treatment include animals, most preferably mammalian species such as humans and domestic animals such as dogs, cats, horses, and the like. Preferred forms for the administration of Compound I include Form N-2, Form N-1, and the HCl salt of Form N-1; and more preferably, Form N-2.

Exemplary compositions for oral administration include suspensions comprising particles of Compound I in one or more of the forms disclosed herein dispersed in a liquid medium. Preferably, the suspension comprises Compound I in Form N-2, Form N-1, and the HCl salt of Form N-1; and more preferably, in Form N-2. The suspension may further comprise, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate, and/or lactose and/or other excipients, binders, extenders, disintegrants, diluents, and lubricants such as those known in the art. Compound I in Form N-2, Form N-1, and/or the HCl salt of Form N-1 also may be delivered by sublingual and/or buccal administration, e.g. with molded, compressed, or freeze-dried tablets. Exemplary compositions may include fast-dissolving diluents such as mannitol, lactose, sucrose, and/or cyclodextrins. Also, included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (CARBOPOL 934®). Lubricants, glidants, flavors, coloring agents, and stabilizers may also be added for ease of fabrication and use.

Typically, the solid form of a pharmaceutically active material is important in the preparation of a solid dosage form, such as tablets or capsules as the manufacturing, stability, and/or the performance of the pharmaceutically active material can be dependent upon the solid form. Generally, a crystalline form provides pharmaceutically active material with uniform properties, such as solubility, density, dissolution rate, and stability. In the present invention, Compound I in Form N-2, Form N-1, and/or the HCl salt of Form N-1 has properties suitable for the manufacture of tablets or capsules, for providing a stable oral dosage form, and/or for delivery of Compound I to a patient in need thereof.

Methods of Preparation and Characterization

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by microcrystallization of solutions. Care should be taken that milling or micronizing of crystals does not result in any change in crystallinity from the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, powder x-ray diffraction, or the like, to assure formation of the preferred crystalline form of the product. The resulting crystalline form may be produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Crystalline forms may be prepared directly from the reaction medium of the final process for preparing Compound I. This may be achieved, for example, by employing in the final process step a solvent or a mixture of solvents from which Compound I may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one crystalline form and/or polymorph in a sample may be determined by techniques such as powder x-ray diffraction (PXRD) or solid state nuclear magnetic resonance spectroscopy. For example, the presence of extra peaks in the comparison of an experimentally measured PXRD pattern with a simulated PXRD pattern may indicate more than one crystalline form and/or polymorph in the sample. The simulated PXRD may be calculated from single crystal x-ray data. see Smith, D. K., "*A FORTRAN Program for Calculating X-Ray Powder Diffraction Patterns*," Lawrence Radiation Laboratory, Livermore, Calif., UCRL-7196 (April 1963).

Crystalline forms of Compound I according to the invention may be characterized using various techniques, the operation of which are well known to those of ordinary skill in the art. The crystalline forms of Compound I may be characterized and distinguished using single crystal x-ray diffraction performed under standardized operating conditions and temperatures, which is based on unit cell measurements of a single crystal of the form at a fixed analytical temperature. The approximate unit cell dimensions in Angstroms (Å), as well as the crystalline cell volume, space group, molecules per cell, and crystal density may be measured, for example at a sample temperature of 25° C. A detailed description of unit cells is provided in Stout & Jensen, X-Ray Structure Determination: A Practical Guide, Macmillan Co., New York (1968), Chapter 3, which is herein incorporated by reference.

Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, preferably both run at the same analytical temperature, and measurements for the subject form characterized as a series of 2θ values (usually four or more).

Other means of characterizing the form may be used, such as solid state nuclear magnetic resonance (NMR), differential scanning calorimetry, thermography, and gross examination of the crystalline or amorphous morphology. These parameters may also be used in combination to characterize the subject form.

The crystalline forms were analyzed using one or more of the testing methods described below.

Single Crystal X-Ray Measurements

Data were collected on a Bruker-Nonius CAD4 serial diffractometer (Bruker AXS, Inc. Madison, Wis.). Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. and Minor, W., in *Macromolecular Crystallography*, eds. Carter, W. C. Jr and Sweet, R. M., Academic Press, NY, 1997) in the Collect program suite (Collect: Data collection software, R. Hooft, Nonius B. V., 1998). When indicated, crystals were cooled in the cold stream of an Oxford Cryosystems Cryostream Cooler (Oxford Cryosystems, Inc., Devens, Mass.) during data collection.

The structures were solved by direct methods and refined on the basis of observed reflections using either the SDP software package (SDP Structure Determination Package, Enraf-Nonius, Bohemia, N.Y.) with minor local modifications or the crystallographic package, maXus (maXus Solution and Refinement Software Suite: S. Mackay, C. J. Gilmore, C. Edwards, M. Tremayne, N. Stewart, and K. Shankland).

The derived atomic parameters (coordinates and temperature factors) were refined through full matrix least-squares. The function minimized in the refinements was $\Sigma_w(|F_{OI}|-|F_C|)^2$. R is defined as $\Sigma||F_O|-|F_C||/\Sigma|F_O|$ while $R_w=[\Sigma_w(|F_O|-|F_C|)^2/\Sigma_w|F_O|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

Simulated powder x-ray diffraction patterns were generated from the single crystal atomic parameters at the data collection temperature, unless noted otherwise.

Powder X-Ray Diffraction Measurements—Method A

About 200 mg were packed by the backloading method into a Philips powder X-ray diffraction (PXRD) sample holder. The sample was transferred to a Philips MPD unit (45 KV, 40 mA, Cu Kα). Data were collected at room temperature in the 2 to 32 2-theta range (continuous scanning mode, scanning rate 0.03 degrees/sec., auto divergence and anti scatter slits, receiving slit: 0.2 mm, sample spinner: ON)

Powder X-Ray Diffraction Measurements—Method B

X-ray powder diffraction data were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for $3 \leq 2\theta \leq 35°$ with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ.

Powder X-Ray Diffraction Measurements—Method C

X-ray powder diffraction (PXRD) data were obtained using a Bruker GADDS (General Area Detector Diffraction System) manual chi platform goniometer. Powder samples were placed in thin walled glass capillaries of 1 mm or less in diameter; the capillary was rotated during data collection. The sample-detector distance was 17 cm. The radiation was Cu Kα ($\lambda$=1.5418 Å). Data were collected for $3<2\theta<35°$ with a sample exposure time of at least 300 seconds.

DSC (Open Pan)

Differential scanning calorimetry (DSC) experiments were performed in a TA Instruments™ model Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA (Open Pan)

Thermal gravimetric analysis (TGA) experiments were performed in a TA Instruments™ model Q500 or 2950. The sample (about 10-30 mg) was placed in a platinum pan, previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

EXAMPLES

Example 1

Neat Form N-2

76 mL of Compound I reaction mixture was charged to a 100 mL three-neck flask, equipped with a mechanical stirrer. The reaction mixture is composed of Compound I, toluene and either 1-propanol or iso-butanol. The solution was distilled to 49 mL under atmospheric pressure. The bath temperature was 130° C. and the final batch temperature was 111° C. The solution was cooled to 87° C. 36 mg of seeds were charged and the batch was cooled from 87° C. to 80° C. over 2 hours. The batch was further cooled from 80° C. to 20° C. over 2 hours and stirring continued at 20° overnight. The slurry was filtered and the wet cake washed with 10 mL of toluene. The wet cake was dried at 50° C. in a vacuum oven overnight. The dried powder weighed 2.98 g (89.1 M %).

Example 2

Neat Form N-1

The N-1 form can be prepared from methanol, ethyl acetate, chloroform, acetonitrile, toluene, tetrahydrofuran, or methyl t-butyl ether. 287 mg of Compound I was dissolved in 0.4 mL of methanol at 50° C. The solution was heated to 65° C. to ensure complete dissolution. The solution was stirred at 65° C. for 30 min., cooled to 20° C. over 90 min., and then stirring continued overnight. The slurry was filtered and the wet cake was dried at 30° C. under vacuum overnight.

Example 3

HCl Salt of N-1 Form 600 mg of Compound I was dissolved in 18 mL of IPA at 50° C. Separately, 136.5 µL of 37% HCl was dissolved in 1 mL IPA. 0.1 mL of the HCl solution was added to the batch and seeded with 6 mg of the HCl salt. The seed did not dissolve. The remaining HCl solution was added to the batch in portions over 5 hours. The batch was stirred at 50° C. for 1 hour and cooled to 20° C. over 1 hours. The slurry was stirred for at least 2 hours at 20° C. The slurry was filtered and the wet cake was washed with 2 mL of IPA. The wet cake was dried at 30° C. under vacuum overnight. The dry powder weighed 0.4 g.

What is claimed is:
1. A crystalline form of Compound I:

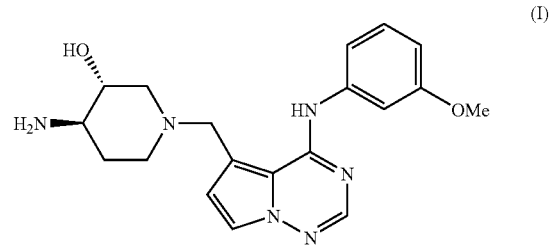

consisting essentially of Form N-2.

2. The crystalline form according to claim 1 consisting of said Form N-2.

3. The crystalline form according to claim 1, wherein said Form N-2 is in substantially pure form.

4. The crystalline form according to claim 1, wherein said Form N-2 is characterized by a simulated powder x-ray diffraction pattern substantially as shown in FIG. 1.

5. The crystalline form according to claim 1, wherein said Form N-2 is characterized by an observed powder x-ray diffraction pattern substantially as shown in FIG. 1.

6. The crystalline form according to claim 1, wherein said Form N-2 is characterized by a powder x-ray diffraction pattern comprising four or more 2θ values (CuKα λ=1.5418 Å) selected from: 10.5±0.1, 13.0±0.1, 13.6±0.1, 15.8±0.1, 16.2±0.1, 16.9±0.1, 20.6±0.1, 21.2±0.1, 21.5±0.1, 24.4±0.1, 28.6±0.1, wherein measurement of said crystalline form is at a temperature of about 25° C.

7. The crystalline form according to claim 1, wherein said Form N-2 is characterized by a powder x-ray diffraction pattern comprising five or more 2θ values (CuKα λ=1.5418 Å) selected from: 10.5±0.1, 13.0±0.1, 13.6±0.1, 15.8±0.1, 16.2±0.1, 16.9±0.1, 20.6±0.1, 21.2±0.1, 21.5±0.1, 24.4±0.1, 28.6±0.1, wherein measurement of said crystalline form is at a temperature of about 25° C.

8. The crystalline form according to claim 1, wherein said Form N-2 is characterized by unit cell parameters substantially equal to the following:

Cell dimensions: a=6.72 Å
   b=10.93 Å
   c=26.12 Å
   α=90.0°
   β=108.5°
   γ=90.0°

Space group: $P2_12_12_1$

Molecules of Compound I/asymmetric unit: 1 wherein measurement of said crystalline form is at a temperature of about 25° C.

9. The crystalline form according to claim 1, wherein said Form N-2 is characterized by one or more of the following:

a) Cell dimensions: a=6.72 Å
   b=10.93 Å
   c=26.12 Å
   α=90.0°
   β=108.5°
   γ=90.0°

Space group: $P2_12_12_1$

Molecules of Compound I/asymmetric unit: 1 wherein measurement of said crystalline form is at a temperature of about 25° C.;

b) a powder x-ray diffraction pattern comprising four or more 2θ values (CuKα λ=1.5418 Å) selected from: 10.5±0.1, 13.0±0.1, 13.6±0.1, 15.8±0.1, 16.2±0.1, 16.9±0.1, 20.6±0.1, 21.2±0.1, 21.5±0.1, 24.4±0.1, 28.6±0.1, wherein measurement of said crystalline form is at a temperature of about 25° C.; and/or c) a thermogravimetric analysis thermogram having negligible weight loss upon heating to a temperature of about 150° C.

10. A crystalline form of Compound I:

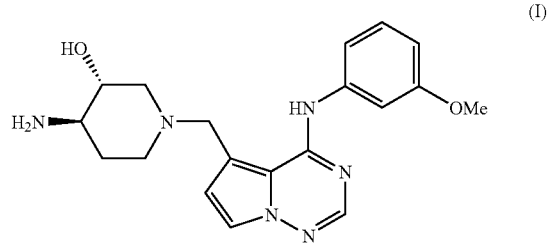

(I)

consisting essentially of Form N-1.

11. The crystalline form according to claim 10, wherein said Form N-1 is characterized by a powder x-ray diffraction pattern comprising four or more 2θ values (CuKα λ=1.5418 Å) selected from: 7.7±0.1, 13.4±0.1, 14.6±0.1, 19.5±0.1 19.8±0.1 20.3±0.1 20.9±0.1, 22.7±0.1, 26.9±0.1, wherein measurement of said crystalline form is at a temperature of about 25° C.

12. The crystalline form according to claim 10, wherein said Form N-1 is characterized by unit cell parameters substantially equal to the following:

Cell dimensions: a=6.72 Å
   b=14.06 Å
   c=19.93 Å
   α=90.0°
   β=90.0°
   γ=90.0°

Space group: $P2_12_12_1$

Molecules of Compound I/asymmetric unit: 1 wherein measurement of said crystalline form is at a temperature of about 25° C.

13. The crystalline form according to claim 10, wherein said Form N-1 is characterized by a melting point in the range of from about 134° C. to about 140° C.

14. A crystalline form of Compound I:

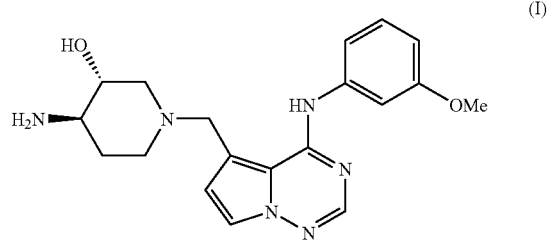

(I)

consistently essentially of the HCl salt of Form N-1.

15. The crystalline form according to claim 14, wherein said HCl salt of Form N-1 is characterized by a powder x-ray diffraction pattern comprising four or more 2θ values (CuKα λ=1.5418 Å) selected from: 5.2±0.1, 11.2±0.1, 16.3±0.1, 16.7±0.1, 19.1±0.1, 22.1±0.1, 23.5±0.1, 27.5±0.1, wherein measurement of said crystalline form is at a temperature of about 25° C.

16. The crystalline form according to claim 14, wherein said HCl salt of Form N-1 is characterized by unit cell parameters substantially equal to the following:

Cell dimensions: a=33.67 Å
 b=7.18 Å
 c=23.51 Å
 α=90.0°
 β=132.4°
 γ=90.0°
Space group: C2
Molecules of Compound I/asymmetric unit: 2 wherein measurement of said crystalline form is at a temperature of about 25° C.

17. The crystalline form according to claim 14, wherein said HCl salt of Form N-1 is characterized by a melting point in the range of from about 230° C. to about 245° C.

18. A pharmaceutical composition comprising the crystalline form according to claim 1 and a pharmaceutically acceptable carrier or diluent.

19. The pharmaceutical composition according to claim 18 wherein said crystalline form is in substantially pure form.

20. A method for treating non-small cell lung cancer or pancreatic cancer, comprising administering to a mammalian species in need thereof, a therapeutically effect amount of Compound I

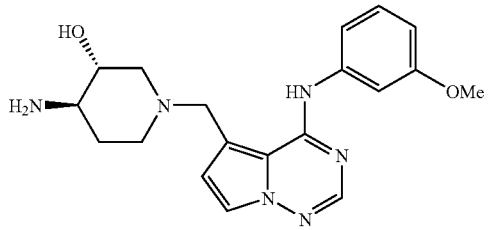

(I)

wherein said Compound I is provided in a crystalline form according to claim 1.

21. A method for treating non-small cell lung cancer or pancreatic cancer, comprising administering to a mammalian species in need thereof, a therapeutically effect amount of Compound I

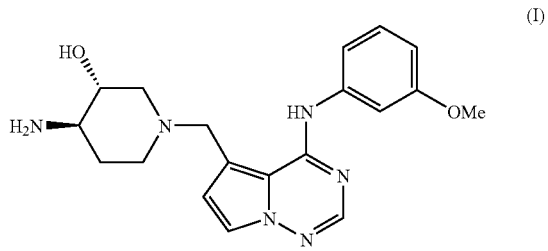

(I)

wherein said Compound I is provided in a crystalline form according to claim 10.

22. A method for treating non-small cell lung cancer or pancreatic cancer, comprising administering to a mammalian species in need thereof, a therapeutically effect amount of Compound I

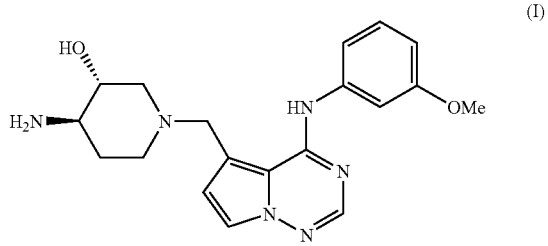

(I)

wherein said Compound I is provided in a crystalline form according to claim 14.

* * * * *